(12) United States Patent
Howard et al.

(10) Patent No.: US 11,195,601 B2
(45) Date of Patent: Dec. 7, 2021

(54) CONSTRUCTING PREDICTION TARGETS FROM A CLINICALLY-DEFINED HIERARCHY

(71) Applicant: International Business Machines Corporation, Armonk, NY (US)

(72) Inventors: Kathryn L. Howard, Boston, MA (US); Hyuna Yang, Somerville, MA (US); Gigi Yuen-Reed, Tampa, FL (US)

(73) Assignee: International Business Machines Corporation, Armonk, NY (US)

( * ) Notice: Subject to any disclaimer, the term of this patent is extended or adjusted under 35 U.S.C. 154(b) by 546 days.

(21) Appl. No.: 15/609,782

(22) Filed: May 31, 2017

(65) Prior Publication Data

US 2018/0349559 A1 Dec. 6, 2018

(51) Int. Cl.
| | | |
|---|---|---|
| *G16H 10/60* | (2018.01) | |
| *G06N 20/00* | (2019.01) | |
| *G16H 40/63* | (2018.01) | |
| *G16H 40/20* | (2018.01) | |
| *G16H 50/30* | (2018.01) | |
| *G16H 50/50* | (2018.01) | |

(Continued)

(52) U.S. Cl.
CPC .............. *G16H 10/60* (2018.01); *G06N 5/022* (2013.01); *G06N 20/00* (2019.01); *G16H 40/20* (2018.01); *G16H 40/63* (2018.01); *G16H 50/20* (2018.01); *G16H 50/30* (2018.01); *G16H 50/50* (2018.01)

(58) Field of Classification Search
None
See application file for complete search history.

(56) References Cited

U.S. PATENT DOCUMENTS 7,702,598 B2    4/2010    Saidi et al.
7,921,068 B2    4/2011    Guyon et al.
(Continued)

OTHER PUBLICATIONS

Adler Perotte, Rimma Pivovarov, Karthik Natarajan, Nicole Weiskopf, Frank Wood, Noémie Elhadad, Diagnosis code assignment: models and evaluation metrics, Journal of the American Medical Informatics Association, vol. 21, Issue 2, Mar. 2014, pp. 231-237 (Year: 2013).*

(Continued)

*Primary Examiner* — Robert W Morgan
*Assistant Examiner* — Andrew E Lee
(74) *Attorney, Agent, or Firm* — Steven Bouknight; Edell, Shapiro & Finnan, LLC (57) ABSTRACT

A method, a computing system and a computer program product are provided. A model is generated and trained. The model is based on clinical data with outcomes from clinically-defined hierarchical metadata in a selected level of clinically-defined hierarchical metadata serving as an initial set of prediction targets. A score is determined for each of the prediction targets based on the generated model and the set of evaluation factors. The set of prediction targets, the generated model, and the scores for the set of prediction targets are updated until the updated scores for the updated set of prediction targets satisfy acceptance criteria. The updated generated model, using the updated set of prediction targets, is applied to predict one of a set of updated prediction targets of mutually exclusive outcome categories.

9 Claims, 3 Drawing Sheets

(51) Int. Cl.
*G16H 50/20* (2018.01)
*G06N 5/02* (2006.01)

(56) References Cited

U.S. PATENT DOCUMENTS

| | | | |
|---|---|---|---|
| 8,131,475 | B2 | 3/2012 | Staudt et al. |
| 8,714,983 | B2 | 5/2014 | Kil |
| 8,731,966 | B2 | 5/2014 | Breitenstein et al. |
| 8,819,024 | B1 * | 8/2014 | Toderici ............... G06F 16/36 707/740 |
| 9,028,405 | B2 | 5/2015 | Tran |
| 9,200,324 | B2 | 12/2015 | Cavet et al. |
| 10,600,406 | B1 * | 3/2020 | Shapiro ............... G06F 16/36 707/740 |
| 2004/0122705 | A1 | 6/2004 | Sabol et al. |
| 2004/0122707 | A1 | 6/2004 | Sabol et al. |
| 2004/0122719 | A1 | 6/2004 | Sabol et al. |
| 2008/0120593 | A1 * | 5/2008 | Keren ............... G06F 9/451 717/105 |
| 2008/0275732 | A1 * | 11/2008 | Falchuk ............... G06F 19/00 705/3 |
| 2010/0306272 | A1 * | 12/2010 | Williamson .......... G06F 16/282 707/802 |
| 2014/0279754 | A1 * | 9/2014 | Barsoum ............... G06N 7/005 706/12 |
| 2015/0100336 | A1 | 4/2015 | Ford et al. |
| 2015/0339572 | A1 * | 11/2015 | Achin ............... G06N 5/02 706/46 |
| 2016/0063179 | A1 | 3/2016 | Huh et al. |
| 2018/0060513 | A1 * | 3/2018 | Tang ............... G16H 40/63 |
| 2018/0060738 | A1 * | 3/2018 | Achin ............... G06Q 10/04 |
| 2018/0182474 | A1 * | 6/2018 | Erdmann ............... G06F 19/00 705/3 |

OTHER PUBLICATIONS

De Leeuw et al., "Random Coefficient Models for Multilevel Analysis", Journal of Educational Statistics, 11, 1986, 51 pages.
Longford, "Random Coefficient Models", Oxford University Press, NY, 1993, 9 pages.
Longford, "A Fast Scoring Algorithm for Maximum Likelihood Estimation in Unbalanced Mixed Models with Nested Random Effects", Biometrika, 74:817-827, Educational Testing Service, 1987, 30 pages.
Raudenbush et al., "A Hierarchical Model for Studying School Effects". Sociology of Education, vol. 59, No. 1, Jan. 1986, pp. 1-17.
Gelman et al., Bayesian Data Analysis, Third Edition, Texts in Statistical Science, CRC Press, Taylor & Francis Group, LLC, 2014, 656 pages.
Babbar et al., "On Flat versus Hierarchical Classification in Large-Scale Taxonomies", Advances in Neural Information Processing Systems 26, 2013, 9 pages.
Kuo et al., "Mining Surprising Patterns and Their Explanations in Clinical Data", Applied Artificial Intelligence, Mar. 2013, 37 pages.
English Abstract of: Yang et al., "Applied research of high-dimensional data mining technology on clinical anomalies identification", Computer Engineering and Design, vol. 34 No. 11, Nov. 2013, pp. 4057-4061.
English Abstract of: Ferreira et al., "Data Mining and Decision Support Systems for Clinical Application and Quality of Life", 2015 10th Iberian Conference on Information Systems and Technologies, CISTI 2015, Jan. 2015, 7 pages.

* cited by examiner

CONSTRUCTING PREDICTION TARGETS FROM A CLINICALLY-DEFINED HIERARCHY

BACKGROUND

Field of the Invention

Present invention embodiments are related to systems, methods and computer program products for constructing a mutually exclusive set of prediction targets from clinically-defined hierarchical metadata. In particular, the present invention embodiments are related to constructing a mutually exclusive set of prediction targets at a correct level of granularity such that a most useful level of information is predicted in view of statistical limitations.

Description of Related Art

There is an increasing demand for predictive modeling in a number of areas such as, for example, healthcare. Many healthcare data systems have a hierarchical structure, such that an instance within the hierarchical structure may belong to multiple hierarchically-organized classes simultaneously. For example, International Classification of Disease, ninth revision, (ICD-9) classifies diagnostic and procedure codes. Multilevel Clinical Classification Software (CCS) classifies ICD-9 codes into categories at different levels of granularity. To determine a most appropriate set of prediction targets (i.e., outcome variables) from a hierarchical structure, a number of things may be considered, including but not limited to, clinical meaningfulness of targets and predictive power of a model with respect to each of the targets. As a result, predicting into a multilevel system and interpreting prediction results can be challenging.

SUMMARY

In an embodiment, a method is provided for generating a set of prediction targets from clinically-defined hierarchical metadata. A computer system generates and trains a model based on clinical data with outcomes from a selected level of the clinically-defined hierarchical metadata serving as an initial set of prediction targets. The computer system determines a score for each prediction target in the set of prediction targets based on the generated model and a set of evaluation factors. The set of prediction targets, the generated model, and the scores for the set of prediction targets are updated until the updated scores for the updated set of prediction targets satisfy acceptance criteria. The updated generated model is applied to predict one of the set of updated prediction targets of mutually exclusive outcome categories. This embodiment is advantageous over known solutions because the model need not incorporate a hierarchical structure of outcomes, making modeling simpler. Also, this embodiment is not limited to using a same level of granularity for all of the outcomes. Further, the model is flexible and easily extended. For example, weights in an efficacy score formulation can be adjusted based on a purpose of a classification or on reliability of each component. In addition, an efficacy score function can be designed based on properties of the evaluation factors.

Another aspect of the invention may include updating a prediction target when a score of the prediction target is less than a minimum threshold or the score of the prediction target is less than a score for a new prediction target at a higher level of the clinically-defined hierarchical metadata that includes the prediction target. This aspect of the invention provides a user with a subjective choice in criteria for determining when a prediction target should be updated.

In a third aspect the invention, the set of evaluation factors may include prediction accuracy. Measurements of the prediction accuracy may include area under a curve, sensitivity, specificity, and an $F_1$ score. This aspect of the invention provides a number of ways of measuring prediction accuracy when prediction accuracy is one of the set of evaluation factors.

Other embodiments may include a computer system for generating a set of prediction targets from clinically-defined hierarchical metadata and a computer program product having computer readable program code embodied therewith for execution on at least one processor to configure the at least one processor to generate a set of prediction targets from clinically-defined hierarchical metadata.

BRIEF DESCRIPTION OF THE DRAWINGS

Generally, like reference numerals in the various figures are utilized to designate like components.

DETAILED DESCRIPTION

Present invention embodiments include methods, systems and computer program products for generating a set of prediction targets at an optimal granularity from clinically-defined hierarchical metadata. Choosing a prediction target at a very detailed level of the clinically-defined hierarchical metadata may not result in a good prediction target for a predictive model because, for example, the prediction target (i.e., diagnosis) may not occur frequently and too few occurrences of the diagnosis may exist in training data to effectively train the predictive model to accurately predict an occurrence of the diagnosis. The set of prediction targets may be mutually exclusive items, or possible outcomes, selected from one or more levels of the clinically-defined hierarchical metadata. Choosing a prediction target at too general a level of the clinically-defined hierarchical metadata may not result in a good prediction target for training a predictive model because the prediction target may not be specific enough to be very useful. Present invention embodiments provide a method, a computer system and a computer program product for determining an optimal level of granularity for prediction targets such that the model may be applied to produce meaningful and accurate results for each of the mutually exclusive prediction targets.

Relevant clinically-defined hierarchical metadata may be defined as a basis for a set of prediction targets. Clinically-defined hierarchical metadata may be used for different modeling purposes and may include, but not be limited to, one or more from a group of medical diagnoses, procedures, medications, healthcare providers, geographical locations and medical events, described at different levels of granularity. For example, to predict an occurrence of a diagnosis, a set of diagnosis categories such as the multilevel clinical classification software (CCS) data system may be used. A subset of the CCS diagnosis categories may be chosen from a hierarchical level of the CCS based on the predictability of the categories and whether the categories have clinical action items to prevent adverse diagnoses at a level of granularity of the hierarchical level. To predict possible medication prescriptions, a hierarchy or categorization of medication prescriptions such as, for example, the Anatomical Therapeutic Chemical (ATC) classification system can be used. To predict possible acute events, a set of medical events (e.g., Systematized Nomenclature of Medicine-Clinical Terms (SNOMED CT)) can be used.

Prediction target efficacy scores may be defined as a combination of evaluation factors for evaluating usefulness and effectiveness of a prediction target. Evaluation factors may include, but not be limited to, clinical meaningfulness, prediction accuracy, observed frequency and estimated financial impact. Clinical meaningfulness for a prediction use case may relate to an ability to take positive action with respect to preventing a predicted negative outcome. Prediction accuracy measurements can be an area under a curve (AUC), a sensitivity of a predicted outcome, specificity, or an $F_1$ score (the $F_1$ score is a well-known measure of a test's accuracy), depending on a goal of a predictive model. Efficacy scores may be constructed using a linear or non-linear function of the evaluation factors, based on desired properties of a set of the prediction targets and relationships among the evaluation factors. If composite scores driven by an average of evaluation factors is desired, rather than by extreme values of the evaluation factors, a convex utility function of the evaluation factors would be used.

Figure 1:
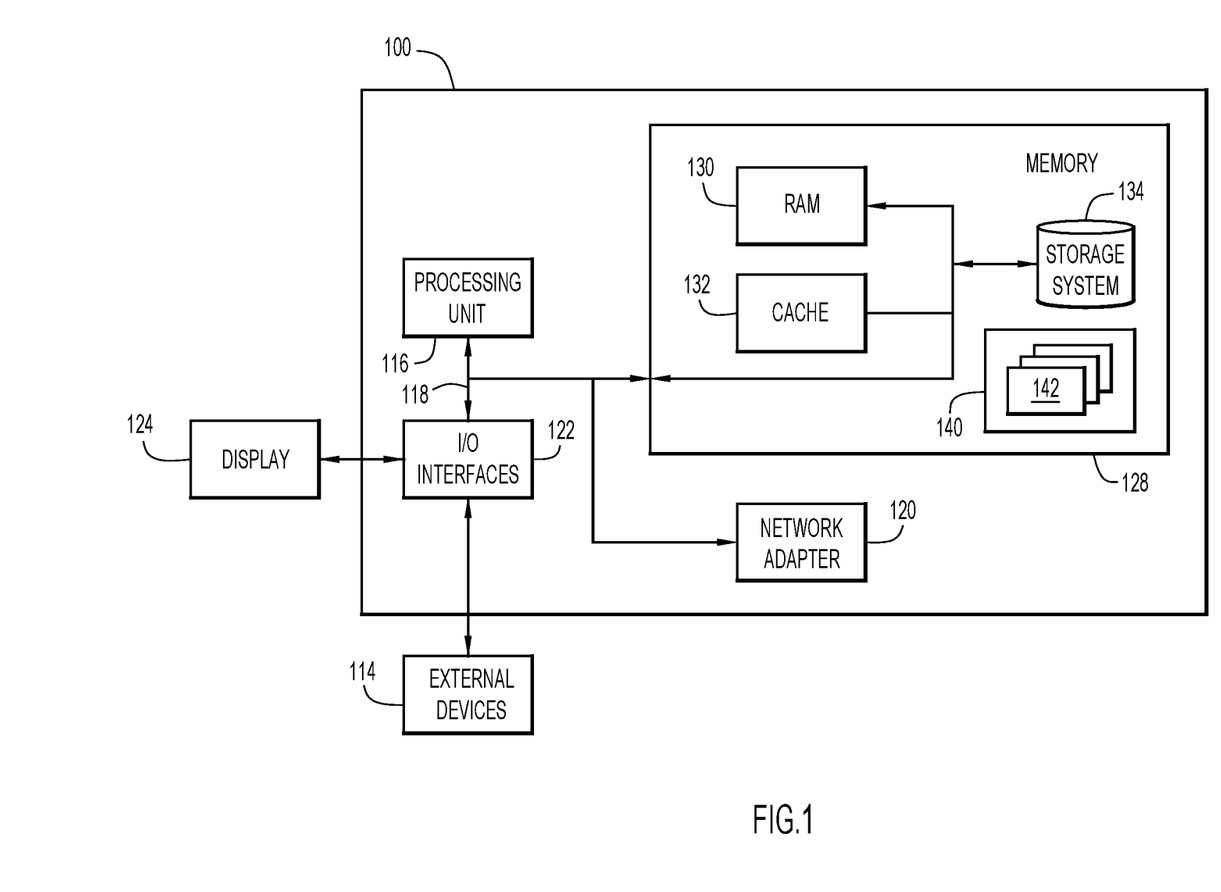
FIG. 1 illustrates an example computer system that may implement various embodiments of the invention.

FIG. 1 shows an example computer system 100 in which various embodiments may be implemented. Computer system 100 is shown in a form of a general-purpose computing device. Components of computer system 100 may include, but are not limited to, one or more processors or processing units 116, a system memory 128, and a bus 118 that couples various system components including system memory 128 to one or more processors 116.

Bus 118 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 100 typically includes a variety of computer system readable media. Such media may be any available media that is accessible by computer system 100, and may include both volatile and non-volatile media, removable and non-removable media.

System memory 128 can include computer system readable media in the form of volatile memory, such as random access memory (RAM) 130 and/or cache memory 132. Computer system 100 may further include other removable/non-removable, volatile/non-volatile computer system storage media. By way of example only, storage system 134 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 118 by one or more data media interfaces. As will be further depicted and described below, memory 128 may include at least one program product having a set (e.g., at least one) of program modules that are configured to carry out the functions of embodiments of the invention.

Program/utility 140, having a set (at least one) of program modules 142, may be stored in memory 128 by way of example, and not limitation, as well as an operating system, one or more application programs, other program modules, and program data. Each of the operating system, the one or more application programs, the other program modules, and the program data or some combination thereof, may include an implementation of a networking environment. Program modules 142 generally carry out the functions and/or methodologies of embodiments of the invention as described herein.

Computing system 100 may also communicate with one or more external devices 114 such as a keyboard, a pointing device, a display 124, etc.; one or more devices that enable a user to interact with computer system 100; and/or any devices (e.g., network card, modem, etc.) that enable computer system 100 to communicate with one or more other computer systems. Such communication can occur via Input/Output (I/O) interfaces 122. Still yet, computer system 100 can communicate with one or more networks such as a local area network (LAN), a general wide area network (WAN), and/or a public network (e.g., the Internet) via network adapter 120. As depicted, network adapter 120 communicates with the other components of computer system 100 via bus 118. It should be understood that, although not shown, other hardware and/or software components could be used in conjunction with computing system 100. Examples, include, but are not limited to: microcode, device drivers, redundant processing units, external disk drive arrays, RAID systems, tape drives, and data archival storage systems, etc.

Figure 2:
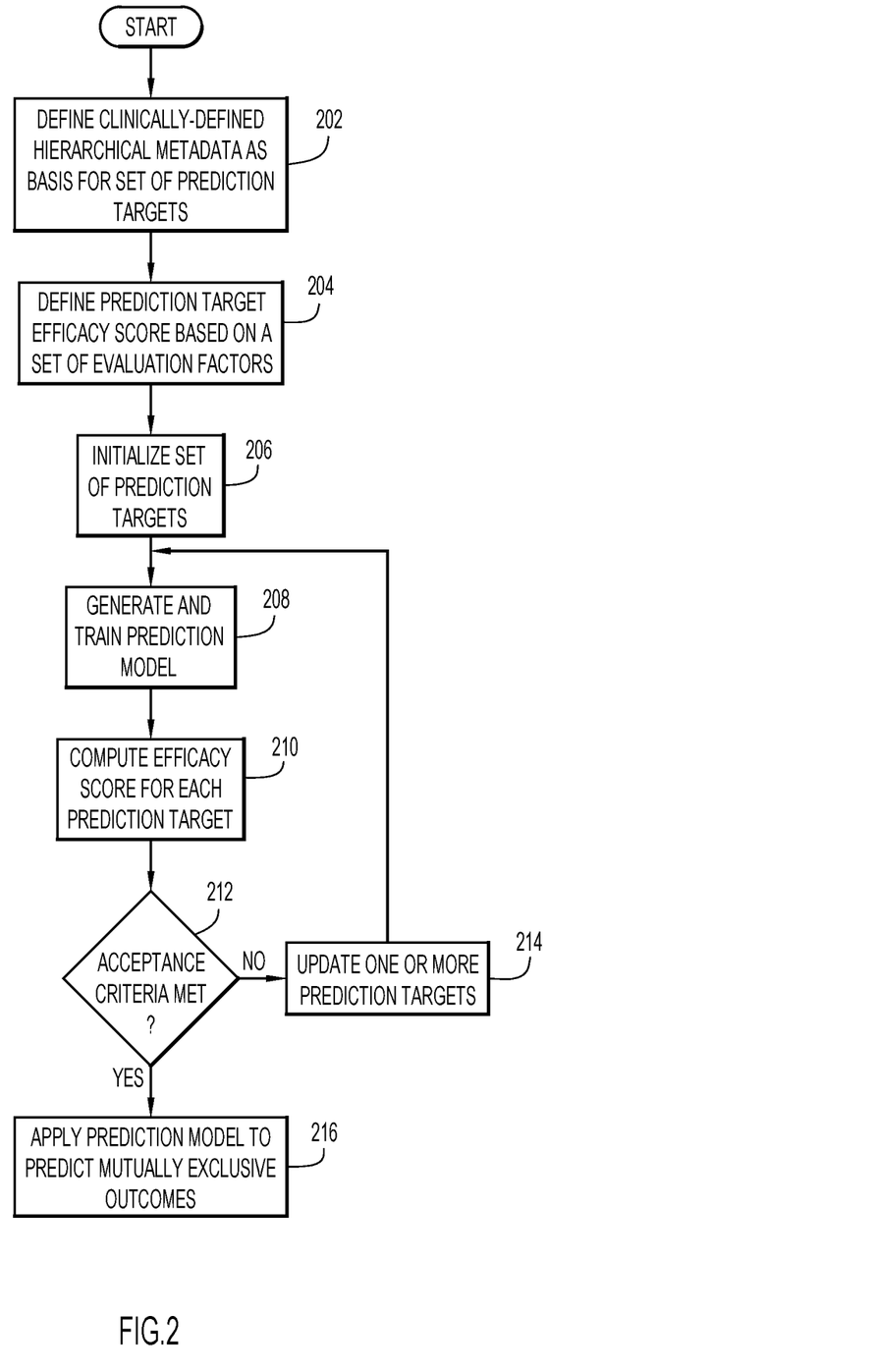
FIG. 2 is a flowchart that illustrates an example process for generating a set of prediction targets from clinically-defined hierarchical metadata in an embodiment.

FIG. 2 is a flowchart that illustrates example processing that may be performed in various embodiments. The process may begin by defining clinically-defined hierarchical metadata as a basis for a set of prediction targets (act 202). This can best be demonstrated by an example.

In the example, a goal is to predict why patients with diabetes will be hospitalized, so that a health care system may take steps to prevent the hospitalizations. Reasons for hospitalization may be analyzed by examining primary diagnoses, which may be recorded as ICD-9 codes. Thus, the set of prediction targets may include a diagnosis and/or a category of diagnoses. There are more than 14,000 ICD-9 codes. Clinical communities have categorized the ICD-9 codes in a meaningful way. For example, multilevel CCS groups ICD-9 codes using a tree-like structure. The multilevel CCS has 18 Level 1 categories, each of which has child categories (Level 2) and grandchild categories (Level 3). For example, one of the Level 1 categories is "Diseases of the circulatory system", which has 5 child categories (Level 2), one of which is "Diseases of the heart". "Diseases of the heart" has 10 child categories (Level 3), one of which is "Heart valve disorders". Multilevel CCS has approximately 400 Level 3 categories. Each child level is more specific than its parent level (i.e., includes a smaller subset of ICD-9 codes from its parent level).

If a reason why a patient with diabetes becomes hospitalized is predicted at Level 3 of the multilevel CCS (the set of prediction targets), the thing predicted (a prediction target or outcome) will be very detailed, but the prediction will be made from among approximately 400 diagnoses. If the prediction is made at Level 1, which is very broad, the set of prediction targets includes only 18 categories of diagnoses. In order to generate a predictive model, which categorizes diabetes patients into diagnosis risk groups, a level for mutually exclusive prediction targets must be decided upon. For some diagnoses, Level 3 would be a good level for making predictions. For other diagnoses, Level 1 would be a good level for making predictions.

Inputs to the predictive model could include medical history (drugs, procedures, conditions, acute events, whether a patient has Type I diabetes, type of insurance, etc.). The inputs could change as a selected level of clinically-defined hierarchical metadata (i.e., prediction targets) changes.

Returning to FIG. 2, a prediction target's efficacy score may be defined based on a set of evaluation factors (act 204). A number of factors can influence a choice of prediction target. Continuing with the above example, two evaluation factors are considered, although there can be many evaluation factors. One evaluation factor may be prediction power. For example, predicting an occurrence of prediction targets (i.e., outcomes) at Level 1 (choosing 1 out of 18 categories of diagnoses) provides better prediction power than predicting occurrences of prediction targets at Level 3 (choosing 1 out of about 400 conditions) due to fewer, more general, possible outcomes at level 1 than at level 3. Another evaluation factor, for this example, could be whether any intervention action items exist. For example, if a physician knows a very specific reason for a hospitalization (e.g., Heart valve disorders) then the physician may know how to prevent the hospitalization. However, if the physician knows only a very broad reason for the hospitalization such as a Level 1 category of diagnoses (e.g., Diseases of the circulatory system), the physician may not know enough about a diagnosis or condition to know how to prevent the hospitalization. For some diagnoses, Level 2 would be a good level for making a prediction. For example, one Level 1 category of diagnoses is "Injury and poisoning" and one child category of diagnoses is "Fractures" (Level 2). "Fractures" has five child diagnoses (Level 3), but all five child diagnoses are treated the same with respect to intervention action items. Therefore, in this example, Level 2 may be best for "Injury and poisoning" conditions. Clinicians may provide advice on which categories do and do not have actionable intervention items. Efficacy score may be defined in a number of different ways, depending on a problem being analyzed. In this example, efficacy score may be defined, for a prediction target (e.g., a diagnosis, a category of diagnoses, a medical condition, a category of medical conditions, etc.) as:

$$\text{efficacy}(X) = (PPV \times \text{Intervention}),$$

where Positive Predictive Value (PPV) is expressed as $$PPV = \frac{\text{\# of patients correctly predicted to have diagnosis } X}{\text{\# of patients predicted to have the diagnosis } X},$$

Intervention = 0 if there is no preventative intervention for $X$ and

Intervention = 1 if there is a preventative intervention for $X$.

Returning to FIG. 2, a computer system may initialize an initial, or first, mutually exclusive set of prediction targets (act 206). The prediction targets may include prediction targets at any level of a hierarchical data system. Previous work or a particular input may help to determine an initial prediction target set. If no previous work and no particular input exists, then a bottom-up approach may be used. With respect to the example, a bottom level, conditions or diagnoses of Level 3 of the Multilevel CCS, may be initialized as the initial prediction target set.

Next, an appropriate prediction model may be generated and trained (act 208). With respect to the example, a predictive model based on logistic regression may be used to predict whether a patient with diabetes will be hospitalized with each diagnosis or condition or category of diagnoses or conditions of the set of prediction targets. Although, other predictive models may be used in other embodiments.

Efficacy scores may be calculated for each condition or diagnosis by the computer system based on the set of prediction targets and the evaluation factors (act 210) as described above. With respect to the example, initially the set of prediction targets is at Level 3, which has about 400 diagnoses.

Next, the computer system may determine whether each of the prediction targets of the set satisfies acceptance criteria (act 212). Some examples of acceptance criteria may include a global threshold for a sum of efficacy scores and a minimal threshold for an efficacy score for each prediction target. When the acceptance criteria includes the global threshold, a sum of all efficacy scores with respect to diagnoses included in a prediction target must be greater than or equal to the global threshold for the prediction target to satisfy the acceptance criteria. When the acceptance criteria includes a minimal threshold, an efficacy score with respect to all diagnoses included in a set of prediction targets must be greater than or equal to the minimal threshold for the prediction target to satisfy the acceptance criteria. With respect to the example, a minimal threshold of 0.3 may be used. That is, to satisfy the acceptance criteria, each prediction target in an acceptable set of prediction targets must have an efficacy score that is greater than or equal to 0.3.

With respect to FIG. 2, if the computer system determines that the acceptance criteria are not met by one or more prediction targets of the set of prediction targets, then the one or more prediction targets of the prediction target set may be updated (rolled up to its parent) (act 214) and acts 208-212 may again be performed. The one or more prediction targets to be rolled up have lowest efficacy scores from among the set of prediction targets.

If, during act 212, the computer system determines that the set of prediction targets meets the acceptance criteria, then the prediction model may be applied to predict occurrences of each of the mutually exclusive prediction targets (i.e., outcomes, which may be a diagnosis) (act 216).

Figure 3:
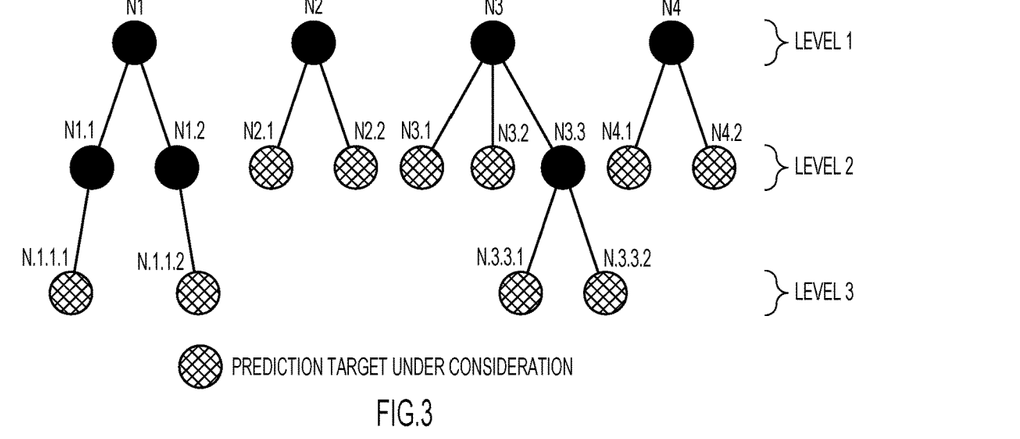
FIGS. 3-5 are hierarchical diagrams illustrating updating of prediction targets, represented by nodes in the Figs., according to an embodiment.
Figure 4:
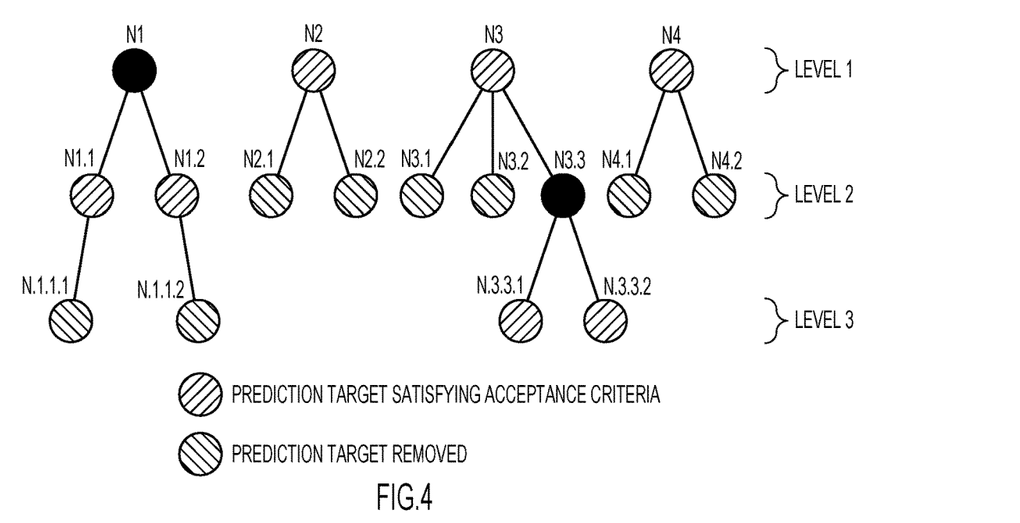

FIG. 3 illustrates an example hierarchical healthcare data set, which may be clinically-defined hierarchical metadata, with a number of nodes, each of which represents a diagnosis or a category of diagnoses. Each of nodes N1, N2, N3 and N4 represent respective Level 1 categories of diagnoses, each of nodes N1.1, N1.2, N2.1, N2.2, N3.1, N3.2, N3.3, N4.1 and N4.2 represent respective Level 2 categories of diagnoses, and each of nodes N1.1.1, N1.1.2, N3.3.1 and N3.3.2 represent a respective Level 3 diagnosis. Level 3 nodes N1.1.1, N1.1.2 and Level 2 nodes N2.1, N2.2, N3.1, N3.2, N3.3.1, N3.3.2, N4.1 and N4.2 may be included in an initial set of prediction targets, as indicated by cross-hatched nodes in FIG. 3. After calculating efficacy scores regarding each of the nodes of the set of prediction targets, nodes N1.1.1, N1.1.2, N2.1, N2.2, N3.1, N3.2, N4.1 and N4.2 are determined to not satisfy the acceptance criteria, while nodes N3.3.1 and N3.3.2 are determined to satisfy the acceptance criteria. Therefore, during act 214 of FIG. 2, nodes N1.1.1 and N1.1.2 may be rolled up into categories of diagnoses of parent node N1.1 and removed from further consideration, nodes N2.1 and N2.2 may be rolled up into categories of diagnoses of parent node N2 and removed from further consideration, nodes N3.1 and N3.2 may be rolled up into categories of diagnoses of parent node N3 and removed from further consideration, and nodes N4.1 and N4.2 may be rolled up into categories of diagnoses of parent node N4 and removed from further consideration. The roll-up of nodes alters the efficacy score because diagnosis codes that were part of a child node become part of a parent node in the set of prediction targets. Because nodes N3.3.1 and N3.3.2 satisfy the acceptance criteria, respective diagnoses represented by nodes N3.3.1 and N3.3.2 will be included in a final prediction target set. FIG. 4 shows N3.3.1 and N3.3.2 as satisfying the acceptance criteria, nodes N1.1, N2, N3 and N4 as being under consideration, and nodes N1.1.1, N1.1.2, N2.1, N2.2, N3.1, N3.2. N4.1 and N4.2 as being removed from further consideration.

Figure 5:
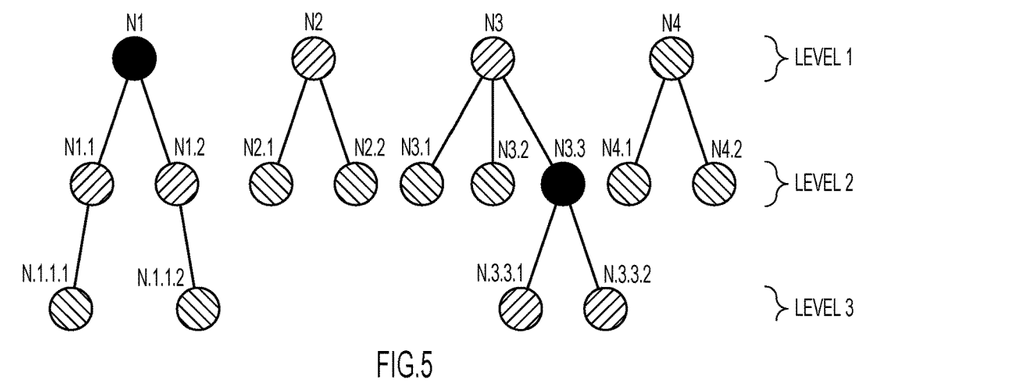

During act 208, a new prediction model may be generated and trained based on the updated prediction targets. During act 210, efficacy scores may be calculated for each of the prediction targets under consideration. During act 212, a determination is made regarding whether the prediction targets under consideration satisfy the acceptance criteria. During this act, nodes N1.1, N1.2, N2 and N3 are determined to satisfy the acceptance criteria and node N4 is removed from further consideration, as shown in FIG. 5. Therefore, nodes N1.1, N1.2, N2 and N3 represent respective categories of diagnoses, which will be included in the final set of prediction targets. Thus, the predicted target set includes nodes N1.1, N1.2, N2, N3 (which includes nodes N3.1 and N3.2, but not node N3.3 and its child nodes), N3.3.1 and N3.3.2.

The above example illustrated a case in which the acceptance criteria included a minimal threshold. When the acceptance criteria uses a global threshold, two different situations should be considered. In situation 1, efficacy scores are not influenced by interdependency between sibling nodes. In situation 2, efficacy scores are influenced by the interdependency between sibling nodes In situation 1, when nodes are rolled up to their respective parent node, each node independently influences the efficacy score of its parent node due to the presence of additional diagnoses, conditions or categories thereof. At each node that does not satisfy the acceptance criteria, that node may be repeatedly rolled up to its parent node and a corresponding efficacy score calculated until a root is reached. A level that has a maximum efficacy score is a final predictor level for that node.

In situation 2, it may be unclear which node or nodes should be rolled-up. One solution may be to roll-up first and third nodes, or second and third nodes, . . . etc. In some cases, an effective approach may be a smart sampling approach, which may include, but not me limited to, Markov Chain Monte Carlo (MCMC).

Embodiments of the invention provide a number of advantages. The advantages include:
 simpler modeling because a model incorporating a hierarchical structure of outcomes is not needed and processing time is enhanced;
 output of the model is a mutually exclusive set of prediction targets with optimal efficacy scores so that one observation has one prediction (i.e., one-to-one mapping), and this one-to-one mapping makes interpretation clear and removes a need for any downstream analysis;
 different levels within the hierarchy can be chosen for different prediction targets, which facilitates selecting prediction targets at a level fit for a particular purpose of a study, thereby reducing processing iterations through the model to enhance processing speed; and
 embodiments can be flexible and easily extended—for example, weights may be included in an efficacy score formulation based on a purpose of a classification or reliability of each component, other functions can be used for efficacy scores based on properties of evaluation factors, and additional factors can be included for evaluating prediction targets.

Results of predictive modeling for a medical condition may be utilized to control various health devices (monitors, administering devices, etc.) to help prevent the medical condition.

The environment of present invention embodiments may include any number of computers or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and may communicate via any suitable communications medium (e.g., LAN, WAN, Intranet, Internet, hardwired, modem connection, wireless, etc.). For example, the functions of the present invention embodiments may be distributed in any manner among the various systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

A communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to a server and/or client systems. The database systems and/or storage structures may be remote from or local to the computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

We claim as our invention:

1. A method for generating a set of prediction targets from clinically-defined hierarchical metadata represented by a hierarchical arrangement of nodes, the method comprising:
   training, by a computer system, a model based on clinical data of patients with a given condition to determine outcome categories, wherein the outcome categories serve as a set of prediction targets for the model and correspond to selected nodes of the clinically-defined hierarchical metadata, wherein each node of the clinically-defined hierarchical metadata corresponds to an outcome category and includes one or more outcomes for the outcome category, and the outcome categories of child nodes provide a greater level of detail than outcome categories for corresponding parent nodes;
   updating, by the computer system, the set of prediction targets and the model until scores for the set of prediction targets satisfy a threshold value, wherein the updating comprises:
      determining, by the computer system, a score for each prediction target in the set of prediction targets based on the trained model, the score being calculated based on a number of correct predictions for the prediction target and existence of a corresponding intervention action for the prediction target;
      identifying each prediction target having a score failing to satisfy the threshold value;
      merging each node corresponding to an identified prediction target having a corresponding parent node into the corresponding parent node, wherein the corresponding parent node includes the one or more outcomes of the node corresponding to the identified prediction target;
      removing each node corresponding to an identified prediction target at a highest level of the clinically-defined hierarchical metadata;
      updating the set of prediction targets with the outcome categories of the merged nodes and the outcome categories of nodes corresponding to prediction targets with scores satisfying the threshold value; and
      training the model based on the set of prediction targets to produce an updated trained model;
   applying, by the computer system, the updated trained model to predict one of the set of prediction targets of outcome categories for a patient with the given condition based on clinical data of the patient; and
   controlling, by the computer system, a health device used by the patient based on the predicted one of the set of prediction targets of the outcome categories to prevent the given condition.

2. The method of claim 1, wherein the clinically-defined hierarchical metadata includes one or more from a categorization of medical diagnoses, procedures, medications, healthcare providers, geographical locations, and medical events.

3. The method of claim 1, further comprising:
   updating a particular prediction target of the set of prediction targets when the score of the particular prediction target is less than a score of a new prediction target at a higher level of the clinically-defined hierarchical metadata including the particular prediction target.

4. A computer system for generating a set of prediction targets from clinically-defined hierarchical metadata represented by a hierarchical arrangement of nodes, the computer system comprising:
   at least one processor;
   a memory; and
   a communication bus connecting the at least one processor and the memory, wherein the at least one processor is configured to perform:
      training a model based on clinical data of patients with a given condition to determine outcome categories, wherein the outcome categories serve as a set of prediction targets for the model and correspond to selected nodes of the clinically-defined hierarchical metadata, wherein each node of the clinically-defined hierarchical metadata corresponds to an outcome category and includes one or more outcomes for the outcome category, and the outcome categories of child nodes provide a greater level of detail than outcome categories for corresponding parent nodes;

updating the set of prediction targets and the model until scores for the set of prediction targets satisfy a threshold value, wherein the updating comprises:
  determining a score for each prediction target in the set of prediction targets based on the trained model, the score being calculated based on a number of correct predictions for the prediction target and existence of a corresponding intervention action for the prediction target;
  identifying each prediction target having a score failing to satisfy the threshold value;
  merging each node corresponding to an identified prediction target having a corresponding parent node into the corresponding parent node, wherein the corresponding parent node includes the one or more outcomes of the node corresponding to the identified prediction target;
  removing each node corresponding to an identified prediction target at a highest level of the clinically-defined hierarchical metadata;
  updating the set of prediction targets with the outcome categories of the merged nodes and the outcome categories of nodes corresponding to prediction targets with scores satisfying the threshold value; and
  training the model based on the set of prediction targets to produce an updated trained model;
applying the updated trained model to predict one of the set of prediction targets of outcome categories for a patient with the given condition based on clinical data of the patient; and
controlling a health device used by the patient based on the predicted one of the set of prediction targets of the outcome categories to prevent the given condition.

5. The computer system of claim 4, wherein the clinically-defined hierarchical metadata includes one or more from a categorization of medical diagnoses, procedures, medications, healthcare providers, geographical locations, and medical events.

6. The computer system of claim 4, wherein the at least one processor is further configured to perform:
  updating a particular prediction target of the set of prediction targets when the score of the particular prediction target is less than a score of a new prediction target at a higher level of the clinically-defined hierarchical metadata including the particular prediction target.

7. A computer program product comprising:
at least one computer readable storage medium having computer readable program code embodied therewith for execution on at least one processor for generating a set of prediction targets from clinically-defined hierarchical metadata represented by a hierarchical arrangement of nodes, the computer readable program code being configured to be executed by the at least one processor to perform:
  training a model based on clinical data of patients with a given condition to determine outcome categories, wherein the outcome categories serve as a set of prediction targets for the model and correspond to selected nodes of the clinically-defined hierarchical metadata, wherein each node of the clinically-defined hierarchical metadata corresponds to an outcome category and includes one or more outcomes for the outcome category, and the outcome categories of child nodes provide a greater level of detail than outcome categories for corresponding parent nodes;
  updating the set of prediction targets and the model until scores for the set of prediction targets satisfy a threshold value, wherein the updating comprises:
    determining a score for each prediction target in the set of prediction targets based on the trained model, the score being calculated based on a number of correct predictions for the prediction target and existence of a corresponding intervention action for the prediction target;
    identifying each prediction target having a score failing to satisfy the threshold value;
    merging each node corresponding to an identified prediction target having a corresponding parent node into the corresponding parent node, wherein the corresponding parent node includes the one or more outcomes of the node corresponding to the identified prediction target;
    removing each node corresponding to an identified prediction target at a highest level of the clinically-defined hierarchical metadata;
    updating the set of prediction targets with the outcome categories of the merged nodes and the outcome categories of nodes corresponding to prediction targets with scores satisfying the threshold value; and
    training the model based on the and set of prediction targets to produce an updated trained model;
  applying the updated trained model to predict one of the set of prediction targets of outcome categories for a patient with the given condition based on clinical data of the patient; and
  controlling a health device used by the patient based on the predicted one of the set of prediction targets of the outcome categories to prevent the given condition.

8. The computer program product of claim 7, wherein the clinically-defined hierarchical metadata includes one or more from a categorization of medical diagnoses, procedures, medications, healthcare providers, geographical locations, and medical events.

9. The computer program product of claim 7, wherein the computer readable program code is further configured to be executed by the at least one processor to perform:
  updating a particular prediction target of the set of prediction targets when the score of the particular prediction target is less than a score of a new prediction target at a higher level of the clinically-defined hierarchical metadata including the particular prediction target.

* * * * *